(12) United States Patent
Coburn et al.

(10) Patent No.: US 7,932,275 B2
(45) Date of Patent: Apr. 26, 2011

(54) 2-AMINOPYRIDINE COMPOUNDS USEFUL AS β-SECRETASE INHIBITORS FOR THE TREATMENT OF ALZHEIMER'S DISEASE

(75) Inventors: Craig A. Coburn, Royersford, PA (US); M. Katharine Holloway, Lansdale, PA (US); Shawn J. Stachel, Perkasie, PA (US)

(73) Assignee: Merck, Sharp & Dohme Corp., Rahway, NJ (US)

( * ) Notice: Subject to any disclaimer, the term of this patent is extended or adjusted under 35 U.S.C. 154(b) by 701 days.

(21) Appl. No.: 11/666,942

(22) PCT Filed: Oct. 25, 2005

(86) PCT No.: PCT/US2005/039932
§ 371 (c)(1),
(2), (4) Date: Oct. 15, 2007

(87) PCT Pub. No.: WO2006/060109
PCT Pub. Date: Jun. 8, 2006

(65) Prior Publication Data
US 2008/0161363 A1    Jul. 3, 2008

Related U.S. Application Data

(60) Provisional application No. 60/623,441, filed on Oct. 29, 2004.

(51) Int. Cl.
*C07D 213/73* (2006.01)

(52) U.S. Cl. .................................. 514/352; 546/311
(58) Field of Classification Search ................. None
See application file for complete search history.

(56) References Cited

U.S. PATENT DOCUMENTS

| 5,540,938 A | 7/1996 | Masterson |
| 6,750,232 B2 * | 6/2004 | Harada et al. ............ 514/334 |
| 6,951,946 B2 | 10/2005 | Kolb |
| 2004/0006082 A1 * | 1/2004 | Harada et al. ............ 514/247 |

FOREIGN PATENT DOCUMENTS

| WO | WO 03/106405 | 12/2003 |
| WO | WO2004/080376 | 9/2004 |
| WO | WO 2005/005374 | 1/2005 |
| WO | WO 2006/065204 | 6/2006 |

OTHER PUBLICATIONS

Hagmann, et al., Bioorg & Med. Chem. Lett., 10 (2000); 1975-1978.

* cited by examiner

*Primary Examiner* — Janet L Andres
*Assistant Examiner* — Heidi Reese
(74) *Attorney, Agent, or Firm* — Keith D. MacMillan; Gerard M. Devlin

(57) ABSTRACT

The present invention is directed to 2-aminopyridine compounds which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

11 Claims, No Drawings

＃ 2-AMINOPYRIDINE COMPOUNDS USEFUL AS β-SECRETASE INHIBITORS FOR THE TREATMENT OF ALZHEIMER'S DISEASE

CROSS-REFERENCE TO RELATED APPLICATIONS

This application claims priority under 35 U.S.C. §119 to U.S. provisional application Ser. No. 60/623,441, filed Oct. 29, 2004.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to a class of novel 2-aminopyridine compounds which are useful as inhibitors of the β-secretase enzyme, and to the treatment of diseases in which the β-secretase enzyme is involved, such as Alzheimer's disease.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a sholt cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_3$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to 2-aminopyridine compounds useful as inhibitors of the β-secretase enzyme, and useful in the treatment of diseases in which the β-secretase enzyme is involved, such as Alzheimer's disease. The invention is also directed to pharmaceutical compositions comprising these compounds, and the use of these compounds and compositions in the treatment of such diseases in which the β-secretase enzyme is involved.

DETAILED DESCRIPTION OF THE INVENTION

The present invention is directed to compounds of formula (I):

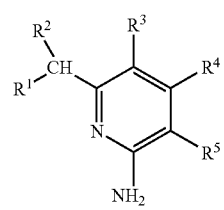

(I)

wherein:
$R^1$ is selected from the group consisting of:
(1) —$C_{1-6}$ alkyl,
(2) —$C_{2-6}$ alkenyl,
(3) —$C_{0-6}$ alkyl-$C_{3-8}$ carbocyclic, wherein one to three of the ring carbon atoms of said carbocyclic group are optionally replaced by one to three ring heteroatoms selected from the group consisting of O, S and N,
(4)

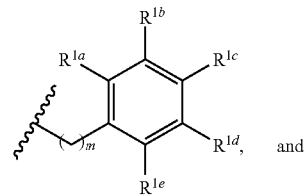

and (5) heteroaryl selected from the group consisting of furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, indazolyl, benzimidazolyl, quinolyl and isoquinolyl,
wherein
(a) said $R^1$ alkyl, alkenyl and cycloalkyl groups are unsubstituted or substituted with one or more halogen, —$C_{1-6}$ alkyl, —$C_{1-6}$ alkoxy, hydroxy or cyano, and
(b) and said $R^1$ heteroaryl group is unsubstituted or substituted with one or more halogen, —$C_{1-6}$ alkyl, —$C_{1-6}$ alkoxy, phenyl, hydroxy or cyano,
and wherein $R^{1a}$, $R^{1b}$, $R^{1c}$, $R^{1d}$ and $R^{1e}$ are selected from the group consisting of:

(a) hydrogen,
(b) halogen,
(c) cyano,
(d) —$C_{1-6}$ alkyl, wherein said alkyl is unsubstituted or substituted with one or more hydroxyl, halogen, or $NH_2$,
(e) —$OR^{7a}$,
(f) —$C(=O)$—$NR^{7a}R^{7b}$,
(g) —NH—$C(=O)$—$R^{7a}$,
(h) —N—$R^{7a}R^{7b}$,
(i) —$S(=O)_p$—$R^8a$
(j) —$NR^{7a}$—$S(=O)_p$—$R^{8a}$,
or $R^{1c}$ and $R^{1d}$ are linked together to form the group —$OCH_2CH_2O$— or —$OCH_2CH_2$—
$R^2$ is selected from the group consisting of:
(1) —$C_{1-6}$ alkyl,
(2) —$C_{2-6}$ alkenyl,
(3) —$C_{1-6}$ alkyl, —$C_{3-8}$ carbocyclic, wherein one to three of the ring carbon atoms of said carbocyclic group are optionally replaced by one to three ring heteroatoms selected from the group consisting of O, S and N,
(4)

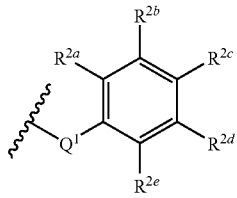

(5) —$(CH_2)_r$-heteroaryl, wherein said heteroaryl is selected from the group consisting of furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, indazolyl, benzimidazolyl, quinolyl and isoquinolyl,
wherein said $R^2$ alkyl, alkenyl, carbocyclic and heteroaryl groups are unsubstituted or substituted with one or more
(a) halogen,
(b) —$C_{1-6}$ alkyl,
(c) —$C_{2-6}$ alkenyl,
(d) —$C_{1-6}$ alkoxy,
(e) —$C_{6-10}$ aryl,
(f) hydroxyl,
(g) cyano, or
(h) —$C(=O)$—$R^{7a}$,
and $R^{2a}$, $R^{2b}$, $R^{2c}$, $R^{2d}$ and $R^{2e}$ are selected from the group consisting of:
(i) hydrogen,
(ii) halogen,
(iii) cyano,
(iv) hydroxyl,
(v) —$C_{0-6}$ alkyl-$C_{3-8}$ cycloalkyl,
(vi) —$C_{1-6}$ alkyl, wherein said alkyl is unsubstituted or substituted with one or more halogen or hydroxyl,
(vii) —$C_{2-6}$ alkenyl,
(viii) —O—$R^{7a}$,
(ix) —$C(=O)$—$R^{7a}$,
(x) —$NO_2$,
(xi) $C_{6-10}$ aryl, wherein said aryl can be unsubstituted or substituted with one or more (A) halogen,
(B) cyano,
(C) —$C_{1-6}$ alkyl,
(D) —$C_{1-6}$ alkoxy,
(E) —$C(=O)$—O—$R^{7a}$,
(F) —$C(=O)$—$R^{7a}$,
(G) —$NR^{7a}R^{7b}$,
(H) —$NR^{7a}$—$S(=O)_p$—$R^{8a}$,
(I) —$NR^{7a}$—$C(=O)$—$R^{7b}$,
(J) —$NO^2$
(x) heteroaryl selected from the group consisting of furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, indazolyl, benzimidazolyl, quinolyl and isoquinolyl,
wherein said heteroaryl is unsubstituted or substituted with one or more halogen, —$C_{1-6}$ alkyl, —$C_{1-6}$ alkoxy, hydroxy or cyano,
or $R^{2c}$ and $R^{2d}$ are linked together to form a group —$CR^{7a}R^{7b}CR^{7c}CR^{7d}CR^{7e}$ $R^{7f}$—, —$OCH_2CH_2O$— or —$OCH_2CH_2$—, and
$Q^1$ is —$C_{1-4}$ alkyl,
$R^3$, $R^4$ and $R^5$ are independently selected from the group consisting of:
(1) hydrogen
(2) -$(Q^2)_n$-$R^9$
(3) heteroaryl wherein said heteroaryl is selected from the group consisting of furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, indazolyl, benzimidazolyl, quinolyl and isoquinolyl,
(4) —$C_{6-10}$ aryl
(5) a carbocyclic group having from 3 to 8 ring atoms, optionally having (i) a —$C(=O)$ ring atom, (ii) from one to three ring heteroatoms selected from the group consisting of S, N and O, and (iii) a single carbon-carbon double bond,
(6) halogen,
(7) cyano,
(8) —$N_3$,
(9) —$NO_2$,
(10) —$OR^{7a}$
wherein $R^9$ is selected from the group consisting of
(a) —$C_{1-10}$ alkyl
(b) —$C_{0-3}$ alkyl-$C_{3-8}$cycloalkyl
(c) —$C_{2-10}$ alkenyl,
(d) —$C_{2-10}$ alkynyl,
(e) —$C_{3-10}$ cycloalkenyl, and
(f) —$C_{3-10}$ cycloalkynyl,
$Q^2$ is selected from the group consisting of O, S, $NR^{7a}$, —$C(=O)$—O—, —$NR^{7a}$—$S(=O)_p$—$S(=O)_p$, —$C(=O)$—$NR^{7a}$, —$NR^{7a}$—$C(=O)$—,
wherein said $R^9$ alkyl, alkenyl, alkynyl, cycloalkyl, cycloalkenyl, cycloalkynyl, carbocyclic, aryl and heteroaryl groups are unsubstituted or substituted with one or more,
(a) halogen
(b) cyano,
(c) —$C_{1-6}$ alkyl,
(d) —$C_{2-6}$ alkenyl,
(e) —$C_{2-6}$ alkynyl,
(f) —$OR^{7a}$
(g) —$C(=O)$—O—$R^{7a}$,
(h) —$C(=O)$—$R^{7a}$,
(i) —$C(=O)$—$NR^{7a}R^{7b}$,
(j) —$NR^{7a}R^{7b}$, (k) —NR$^{7a}$—S(=O)$_p$—R$^{7b}$,
(l) —NR$^{7a}$—C(=O)—R$^{7b}$,
(m) —NO$_2$,
(n) —CH$_2$—C$_{6-10}$ aryl,
(o) —C$_{6-10}$ aryl,
(p) heteroaryl,
(q) —C$_{3-8}$ cycloalkyl
(r) —C(=O)—N—SO$_2$R$^{8a}$,
and said R$^9$ alkyl, alkenyl and alkynyl groups are optionally interrupted with one or more Q$^2$ groups,
R$^{7a}$, R$^{7b}$, R$^{7c}$, R$^{7d}$, R$^{7e}$ and R$^{7f}$ are selected from the group consisting of:
(1) hydrogen,
(2) —C$_{1-6}$ alkyl,
(3) —C$_{3-8}$ cycloalkyl,
(4) —C$_{6-10}$ aryl, and
(5) —CH$_2$—C$_{6-10}$ aryl,
provided that when R$^{7a}$ and R$^{7b}$ are bound to the same N atom, then R$^{7a}$ and R$^{7b}$ may form a four to five hydrocarbon chain with the N atom to which they are attached to form a carbocyclic ring having a single N atom;
wherein said R$^{7a}$-R$^{7f}$ alkyl, cycloalkyl or aryl groups are unsubstituted or substituted with one or more halogen, —C$_{1-6}$ alkyl, —C$_{1-6}$ alkoxy, hydroxyl, cyano, or a carbocyclic group having from 3 to 8 ring atoms, optionally having (i) a —C(=O)— ring atom, (ii) from one to three ring heteroatoms selected from the group consisting of S, N and O, and (iii) a single carbon- carbon double bond,
R$^8$a and R$^{8b}$ are independently selected from the group consisting of
(1) —C$_{1-6}$ alkyl,
(2) —C$_{6-10}$ aryl, and
(3) —CH$_2$—C$_{6-10}$ aryl,
wherein said R$^{8a}$ and R$^{8b}$ alkyl or aryl groups are unsubstituted or substituted with one or more halogen, —C$_{1-6}$ alkyl, —C$_{1-6}$ alkoxy, hydroxyl or cyano;
m is 0 or 1;
n is 0 or 1;
p is 0, 1 or2;
r is 0, 1, 2or3;
and pharmaceutically acceptable salts thereof, and individual enantiomers and diastereomers thereof.
In one embodiment of the compounds of the invention, R$^3$ is hydrogen.
In another embodiment of the compounds of the invention, R$^1$ is

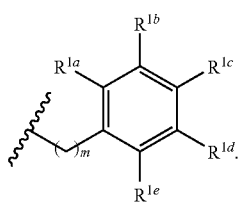

and m is preferably 0. In this embodiment, R$^{1a}$, R$^{1b}$, R$^{1c}$, R$^{1d}$ and R$^{1e}$ are preferably selected from the group consisting of:
(a) hydrogen,
(b) halogen,
(c) —OR$^{8a}$ wherein R$^{8a}$ is C$_{1-6}$ alkyl, and
(d) —CH$_2$OH.
In another preferred group of this embodiment, R$^{1a}$, R$^{1d}$ and R$^{1e}$ are hydrogen, and R$^{1b}$ and R$^{1c}$ are independently selected from the group consisting of:

(a) hydrogen,
(b) halogen,
(c) —OR$^{8a}$ wherein R$^{8a}$ is C$_{1-6}$ alkyl, and
(d) —CH$_2$OH.
In another embodiment of the compounds of the invention, R$^2$ is selected from the group consisting of:

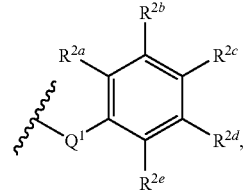

wherein Q$^1$ is preferably CH$_2$. In alternative embodiments, Q$^1$ is a branched C$_3$ or C$_4$ alkyl. R$^{2a}$, R$^{2b}$, R$^{2c}$, R$^{2d}$ and R$^{2e}$ are preferably selected from the group consisting of:
(1) hydrogen,
(2) —C$_{1-6}$ alkyl, wherein said alkyl is unsubstituted or substituted with one or more halogen,
(3) —O—R$^{7a}$, wherein R$^{7a}$ is C$_{1-6}$ alkyl,
(4) —NO$_2$,
(5) C$_{2-6}$ alkenyl,
(6) C$_{1-6}$ alkyl-C$_{3-6}$ cycloalkyl.
In another preferred group of this embodiment, R$^{2a}$, R$^{2b}$, R$^{2c}$, R$^{2d}$ and R$^{2e}$ are each hydrogen.
In another embodiment of the compounds of the invention, R$^4$, R$^5$ and R$^6$ are independently selected from the group consisting of:
(1) hydrogen,
(2) C$_{1-10}$ alkyl,
(3) C$_{6-10}$ aryl, and
(4) halogen.
In a preferred group of this embodiment, R$^4$, R$^5$ and R$^6$ are each hydrogen.
In another embodiment of the compounds of the invention, the invention is directed to compounds of formula (II)

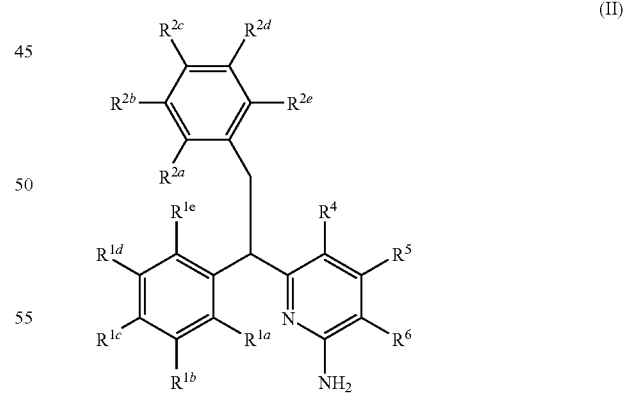

(II)

wherein R$^{1a}$, R$^{1b}$, R$^{1c}$, R$^{1d}$, R$^{1e}$, R$^{2a}$, R$^{2b}$, R$^{2c}$, R$^{2d}$, R$^{2e}$, R$^4$, R$^5$ and R$^6$ are as defined above, and pharmaceutically acceptable salts thereof, and individual enantiomers and diastereomers thereof.
Another embodiment of the present invention includes a compound which is selected from the compounds of the following Examples and pharmaceutically acceptable salts thereof.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkoxy," by itself or as part of another substituent, means the group —O— alkyl, wherein alkyl is defined above, having the number of carbon atoms designated (e.g., $C_{1-6}$ alkoxy means an alkoxy group having from one to six carbon atoms. Exemplary preferred alkoxy groups include methoxy, ethoxy, propoxy, butoxy, sec-butoxy and pentoxy.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated cyclic hydrocarbon radical having the number of carbon atoms designated (e.g., $C_{3-6}$ cycloalkyl means a cycloalkyl group having from three to eight carbon atoms). Exemplary cycloalkyl groups include cyclopropyl, cyclobutyl, cyclopentyl, cyclohexyl and the like.

As used herein, the term "cycloalkenyl," by itself or as part of another substituent, means a cyclic hydrocarbon radical having a single carbon-carbon double bond, and the number of carbon atoms designated (e.g., $C_{3-8}$ cycloalkenyl means a cycloalkenyl group having from three to eight carbon atoms). Exemplary cycloalkenyl groups include cyclopropenyl, cyclobutenyl, cyclopentenyl, and the like.

As used herein, the term "cycloalkynyl," by itself or as part of another substituent, means a cyclic hydrocarbon radical having a single carbon-carbon triple bond, and the number of carbon atoms designated (e.g., $C_{3-8}$ cycloalkynyl means a cycloalkynyl group having from three to eight carbon atoms). Exemplary cycloalkynyl groups include cyclopropynyl, cyclobutynyl, cyclopentynyl, and the like.

As used herein, the term "carbocyclic ring" refers to a saturated or unsaturated hydrocarbon ring radical, and includes cycloalkyl, cycloalkenyl and cycloalkynyl. The term carbocyclic ring as used herein also refers to heterocyclic ring structures, having (i) a —(C═O)— ring atom, (ii) from one to three ring heteroatoms selected from the group consisting of S, N and O, or (iii) a single carbon-carbon double bond. Preferred heterocyclic rings include rings having from three to eight ring atoms, including one to three heteroatoms. Exemplary heterocyclic rings include morpholinyl, pyrrolidinyl, pyrazolidinyl, imidazolidinyl, piperidinyl and piperazinyl.

When a heterocyclic carbocyclic ring as defined herein is substituted, the substituent may be bonded to a ring carbon atom of the heterocyclic group, or to a ring heteroatom which has a valence which permits substitution. Preferably, the substituent is bonded to a ring carbon atom. Similarly, when a heterocyclic carbocyclic ring is defined as a substituent herein, the point of attachment may be to a ring carbon atom of the heterocyclic group, or to a ring heteroatom (i.e., a nitrogen, oxygen or sulfur), which has a valence which permits attachment. Preferably, the attachment is to a ring carbon atom.

As used herein, the term "aryl," by itself or as part of another substituent, means an aromatic or cyclic radical having the number of carbon atoms designated (e.g., $C_{6-10}$ aryl means an aryl group having from six to ten carbons atoms). Preferred aryl groups for use in the invention include phenyl and naphthyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). Exemplary heteroaryl groups for use in the invention include furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, indazolyl, benzimidazolyl, quinolyl and isoquinolyl.

When a heteroaryl group as defined herein is substituted, the substituent may be bonded to a ring carbon atom of the heteroaryl group, or to a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be to a ring carbon atom of the heteroaryl group, or to a ring heteroatom (i.e., a nitrogen, oxygen or sulfur), which has a valence which permits attachment. Preferably, the attachment is at a ring carbon atom.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer of a compound may be obtained by stereoselective synthesis using optically pure starting materials or reagents of known configuration by methods well known in the art.

The compounds claimed in this invention can be prepared according to the following general procedure methods A-D, and the specific examples 1-4.

General Method A:

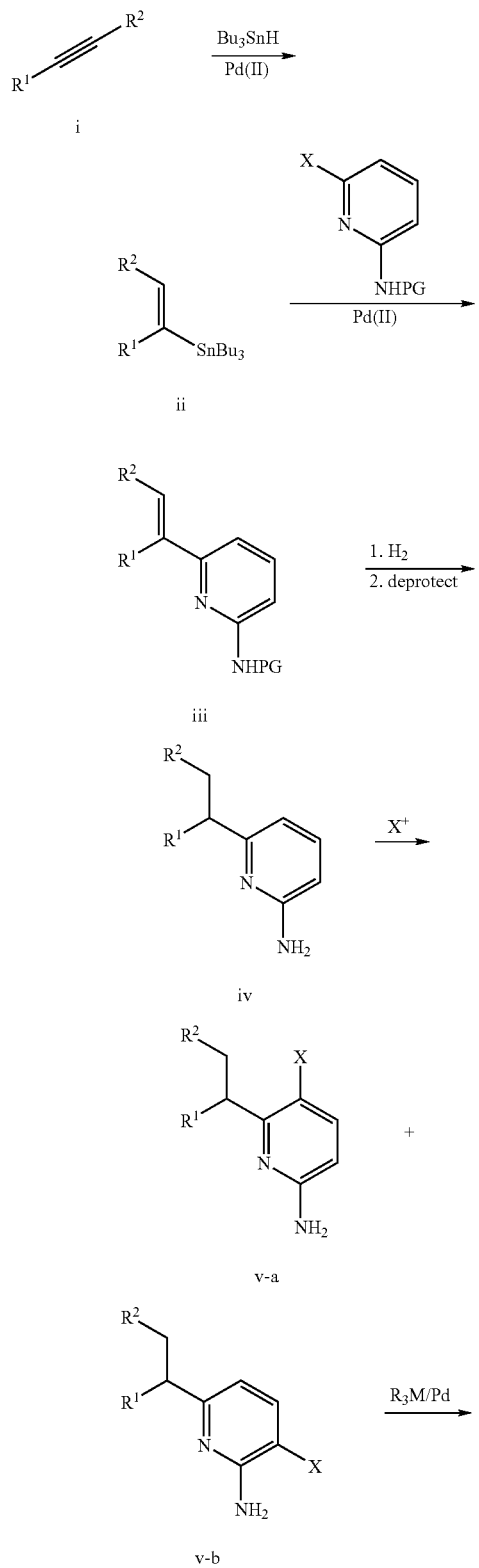

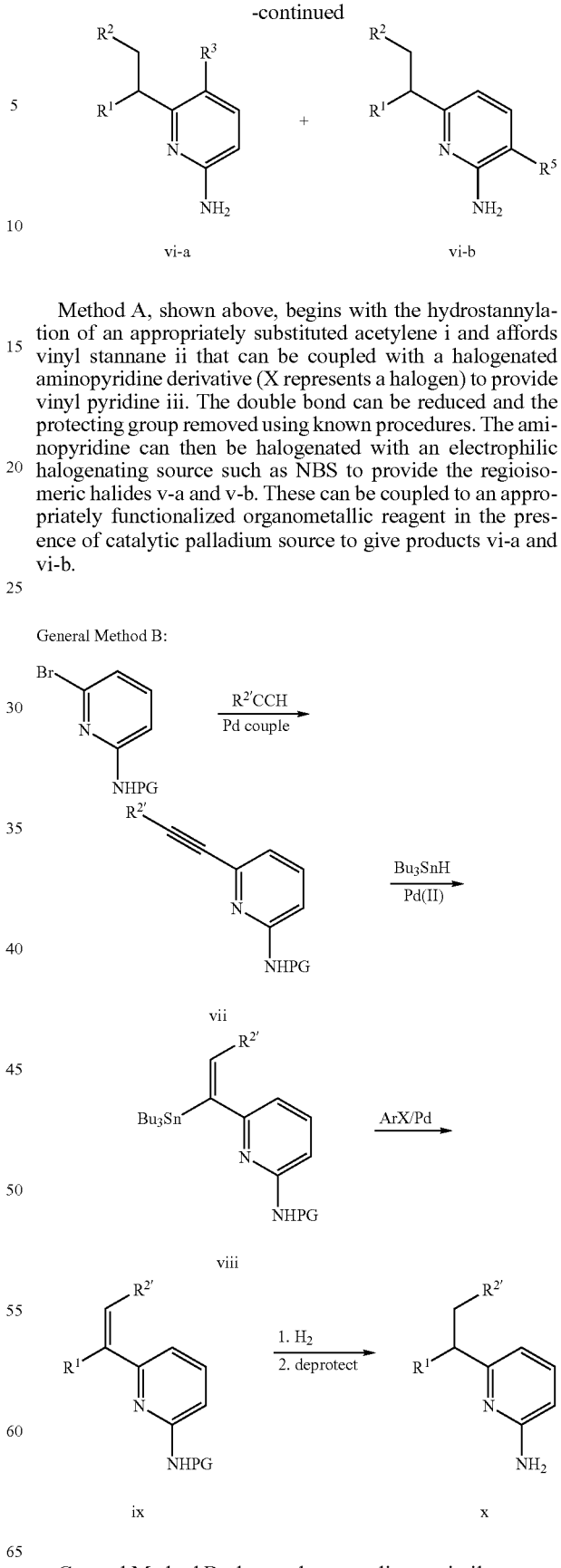

Method A, shown above, begins with the hydrostannylation of an appropriately substituted acetylene i and affords vinyl stannane ii that can be coupled with a halogenated aminopyridine derivative (X represents a halogen) to provide vinyl pyridine iii. The double bond can be reduced and the protecting group removed using known procedures. The aminopyridine can then be halogenated with an electrophilic halogenating source such as NBS to provide the regioisomeric halides v-a and v-b. These can be coupled to an appropriately functionalized organometallic reagent in the presence of catalytic palladium source to give products vi-a and vi-b.

General Method B:

General Method B, shown above, outlines a similar protocol for making compounds wherein $R^2$ is selected from the paragraph (4) group, as described above. The group $R^{2\prime}$ in Method B represents the phenyl moiety of the paragraph (4) $R^2$ group, when Q is $CH_2$. A similar procedure may be used when Q is a branched $C_{1-4}$ alkyl.

Method B begins with the Pd mediated coupling between a protected bromopyridine derivative and a terminal acetylene to afford intermediates vii that can be hydrostannylated with tributyltin hydride and a palladium(II) source. The resulting vinyl stannane vii can be coupled to an aryl halide or aryl triflate in the presence of an appropriate catalyst to afford intermediates ix. The double bond of ix can be hydrogenated and the protecting group removed using the appropriate procedures.

General Method C:

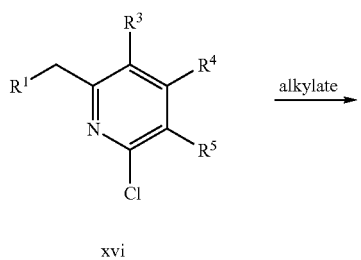

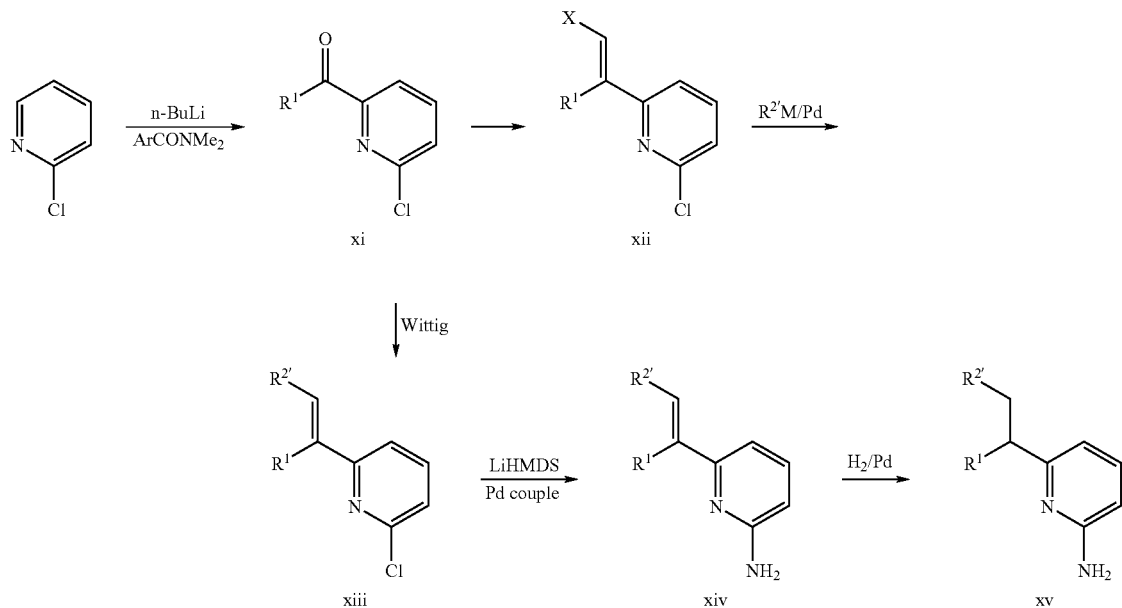

Method C, like Method B, depicts a synthesis of compounds wherein $R^2$ is selected from the paragraph (4) group, as described above. Method C involves the metallation of 2-chloropyridine with n-BuLi and subsequent quenching of the 6-lithioderivative with a reagent that can produce the corresponding ketones xi, such as an N,N-dimethylbenzamide derivative. Olefination of xi using standard Wittig protocols can afford xiii directly or xiii through a two step halo olefination/coupling protocol. Chloropyridine xiii can then be converted to its amino derivative using a palladium mediated amination reaction. Compounds xv can then be formed by reduction of the double bond by catalytic hydrogenation.

General Method D:

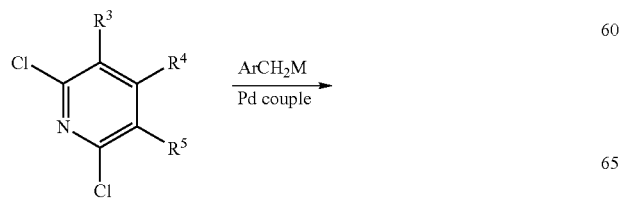

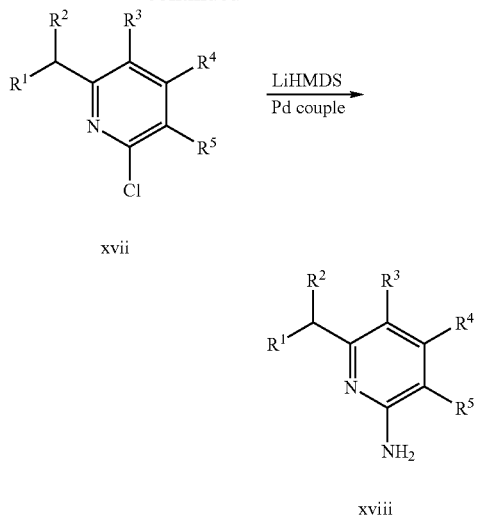

Method D, depicted above, employs the palladium mediated coupling of an appropriately functionalized chloropyridine derivative with a substituted benzyl Grignard reagent or benzyl zinc reagent. Intermediates xvi can be alkylated with a base such as n-BuLi, LDA, or KOtBu to provide xvii. The chloropyridine can then be converted to its amino derivative using a palladium mediated amination reaction.

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, trifluoroacetic, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, ameliorating, controlling or reducing the risk of Alzheimer' s disease. For example, the compounds may be useful for the prevention of dementia of the Alzheimer' s type, as well as for the treatment of early stage, intermediate stage or late stage dementia of the Alzheimer' s type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, for example other beta-secretase inhibitors or gamma-secretase inhibitors; tau phosphorylation inhibitors; blockers of Aβ oligomer formation; p25/CDK5 inhibitors; NK1/NK3 receptor antagonists; HMG-CoA reductase inhibitors; NSAID's including ibuprofen; vitamin E; anti-amyloid antibodies, including anti-amyloid humanized monoclonal antibodies; COX-2 inhibitors; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine and neramexane; $NR^2B$ antagonists; androgen receptor modulators; acetylcholinesterase inhibitors such as galantamine, rivastigmine, donepezil, and tacrine; $mGluR^5$ modulators; growth hormone secretagogues such as ibutamoren, ibutamoren mesylate, and capromorelin; histamine $H_3$ antagonists; AMPA agonists; PDE IV inhibitors; $GABA_A$ inverse agonists; $GABA_A$ α5 receptor ligands; $GABA_B$ receptor ligands; potassium channel blockers; neuronal nicotinic agonists; P-450 inhibitos, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is employed using a biotinylated BACE substrate. The Km of the substrate is greater than 100 μM and can not be determined due to the limit of solubility of the substrate. A typical reaction contains approximately 0.1 nM enzyme, 0.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and is then stopped by the addition of 25 μL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors were prepared starting from 100 μM with three fold series dilution) are included in the reaction mixture (final DMSO concentration is 10%). All experiments are conducted at room temperature using the standard reaction conditions described above. To determine the $IC_{50}$ of the compound, a four parameter equation is used for curve fitting. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and is stopped by the addition of 25 μL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared and the concentration rage was dependent on the potency predicted by ECL) are included in the reaction mixture (final DMSO concentration is 10%). All experiments are conducted at room temperature using the standard reaction conditions described above. To determine the $IC_{50}$ of the compound, four parameters equation is employed for curve fitting. The errors in reproducing the dissociation constants are typically less than two-fold.

The compounds of the following examples had activity in inhibiting the beta-secretase enzyme in the aforementioned assays, generally with an $IC_{50}$ from about 1 nM to 100 μM. Such a result is indicative of the intrinsic activity of the compounds in use as inhibitors of beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Example 1 exemplifies a synthesis according to Method A; example 2 exemplifies a synthesis according to Method B; example 3 exemplifies a synthesis according to Method C; and example 4 exemplifies a synthesis according to Method D.

The following abbreviations are used throughout the text:

Me: methyl
Et: ethyl
Bu: butyl
Ar: aryl
Ph: phenyl
Ac: acetyl
PG: protecting group
DMF: N,N'-dimethyl formamide
THF: tetrahydrofuran
DMSO: dimethylsulfoxide
EDTA: ethylene diamine tetraacetic acid
BSA: bovine serum albumin
CHAPS: 3-[(3-cholamidopropyl)dimethylammonio]-2-hydroxy-1-propanesulfonate
TEA: triethylamine
NBS: N-bromo succinimide
TBAF: tetrabutylammonium fluoride
TFA: trifluoroacetic acid
n-BuLi: n-butyllithium
LDA: lithium diisopropylamide
KOtBu: potassium tert-butoxide
LiHMDS: lithium bis(trimethylsilyl)amide
rt: room temperature
STP: standard temperature and pressure
HPLC: high pressure liquid chromatography
LCMS: liquid chromatography mass spectrometry

EXAMPLE 1

6-(1,2-diphenylethyl)-5-phenylpyridin-2-amine

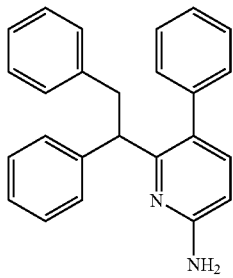

Step A. To a solution containing 1.78 g (10.0 mmol) of diphenylacetylene and 0.071 g (11.0 mmol) of dichlorobis(triphenylphoshine)palladium(II) in 15 mL of THF was added 2.95 mL of tributyltin hydride dropwise at room temperature. The dark brown mixture was stirred for 90 min then concentrated and chromatographed (Hexanes) to afford the desired vinyl stannane as a colorless oil. $^1$H NMR (CDCl$_3$) δ 7.27-6.95 (m, 10H), 6.65 (s, 1H), 1.51 (m, 6H), 1.25 (m, 6H), 0.95 (m, 6H), 0.84 (m, 9H).

Step B. To a degassed solution of the vinyl stannane from step A (350 mg, 0.747 mmol) and 128 mg (0.498 mmol) of 6-bromo-2-pivaloylaminopyridine (reference) in 4 mL of DMF was added 5.0 mg (0.020 mmol) of dichlorobis(acetonitrile)palladium(II). The resulting reaction mixture was heated over 18 h before it was cooled and concentrated. The dark residue was chromatographed (4:1 Hexane/EtOAc) to afford of the desired olefin as a white solid. LCMS (M+1)=357.20.

Step C. A solution containing 1.0 g (2.81 mmol) of the olefin from step B in 50 mL of 1:1 methanol/THF was hydrogenated at STP using 1.0 g of 10% Pd on carbon. After 5 h the catalyst was removed by filtration and the filtrate was evaporated to an oil that was used without further purification. LCMS (M+1)=359.21. This oil was redissolved in 30 mL of TEF and 30 mL of 3N HCl and heated at 70° C. over 50 h. The reaction mixture was cooled and the THF was removed in vacuo. Solid NaOH pellets were added (pH=10) and the resulting mixture was extracted with dichloromethane (3×30 mL). The organics were combined, dried over MgSO$_4$ and chromatographed (1:2 EtOAc/Hex) to afford of the desired aminopyridine as a white solid. LCMS (M+H)=275.24. $^1$H NMR (CDCl$_3$) δ 7.41-7.03 (m, 10H), 6.48 (d, J=6.8 Hz, 1H), 6.26 (d, J=6.8 Hz, 1H), 4.61 (bs, 2H), 4.19 (t, J=8.0 Hz, 1H), 3.55 (dd, J=14, 7.5 Hz, 1H), 3.25 (dd, J=14, 9.5 Hz, 1H).

Step D. A solution of the aminopyridine from step C (170 mg, 0.62 mmol) in 4 mL of DMF was treated with 110 mg (0.62 mmol) of NBS and the reaction mixture was stirred for 30 min. The reaction mixture was diluted with 50 mL of ether and washed with water (7×10 mL) then brine. The organic phase was dried over MgSO4 and evaporated to leave an oil that was purified by column chromatography (2:1 Hex/EtOAc) to afford the 5-bromo derivative. $^1$H NMR (CDC$_{l3}$) δ 7.41-7.08 (m, 11H), 6.18 (d, J=7.2 Hz, 1H), 4.69 (t, J=8.0 Hz, 1H), 4.41 (bs, 2H), 3.61 (dd, J=14, 7.5 Hz, 1H), 3.32 (dd, J=14, 9.5 Hz, 1H).

Step E. A solution containing 90.0 mg (0.255 mmol) of the bromide from step D and 140 mg (0.382 mmol) of phenyltributyltin in 2 mL of DMF was degassed and treated with 18.0 mg (0.025 mmol) of dichlorobis(triphenylphoshine)palladium(II). The resulting reaction mixture was heated at 100° C. for 18 h before it was cooled and diluted with 20 mL of ether. The organic mixture was washed with water (7×3 mL) then brine. Column chromatography (1:1 Hexanes/EtOAc) and treatment of the clean fractions with excess HC$_1$ in ether (1M) afforded the desired aminopyridine hydrochloride salt as a white solid. LRMS (M+H)= 351.20. $^1$H NMR (CD$_3$OD) δ 7.64 (d, J=9.0 Hz, 1H), 7.41-7.18 (m, 11H), 6.97 (m, 2H), 6.88 (d, J=9.0 Hz, 1H), 6.78 (m, 2H), 4.69 (dd, J=10.2, 6.3 Hz, 1H), 3.52 (m, 1H), 3.30 (bt, J=1.5 Hz, 1H).

EXAMPLE 2

6-[1-(3,4-dimethoxyphenyl)-2-phenylethyl]pyridin-2-amine

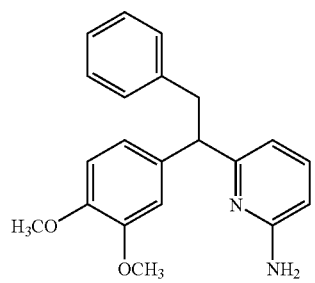

Step A. To a solution of 6-bromo-2-pivaloylaminopyridine (1.0 g, 3.89 mmol) in n-propylamine under nitrogen was added phenyl acetylene (0.427 mL, 3.89 mmol) and tetrakis(triphenylphosphine)palladium(0) (90.0 mg, 0.078 mmol). After heating at 60° C. for 17 h the reaction mixture was cooled and concentrated. The crude material was chromatographed with a 9:1 Hexanes/EtOAc to 100% EtOAc to afford 980 mg of the desired alkyne. LCMS (M+H)=279.

Step B. The alkyne from step A (0.47 g, 1.69 mmol) and dichlorobis(triphenylphosphine) palladium(II) (12 mg, 0.017 mmol) were dissolved in dry THF (5 mL) followed by the dropwise addition of the tri-n-butyltin hydride (0.501 mL, 1.86 mmol). The reaction was stirred at ambient temperature for 16 h, concentrated and loaded onto a silica column. Elution with a gradient of hexanes to 9:1 hexanes/EtOAc afforded the two regioisomeric stannanes in a 1:1 mixture. The less polar isomer was found to be the desired compound. LCMS (M+H)=571.33. $^1$H NMR (CDC$_{13}$) δ 7.94 (d, J=8.15, 1H), 7.92 (s, 1H), 7.45 (t, 1H), 7.15 (m, 3H), 7.06 (m, 2H), 6.82 (s, 1H), 6.66 (d, J=7.51, 1H), 1.49 (m, 6H), 1.31 (m, 16H), 0.97 (m, 5H), 0.87 (m, 9H).

Step C. To a degassed solution of the stannane from step B (108 mg, 0.19 mmol), 4-bromoveratrole (41 mg, 0.19 mmol) and 1.0 mL of DMF was added 13.3 mg (0.019 mmol) of dichlorobis(triphenylphosphine)palladium(II) (10%). After heating at 95° C. for 16 hours the reaction mixture was cooled and loaded directly onto a silica column (7:3 Hexanes/EtOAc to EtOAc) to afford the desired intermediate. LCMS (M+H)=417.17.

Step D. The alkene from step C (50.0 mg, 0.12 mmol) and 50 mg of 10% Pd on carbon was dissolved in 1:1 EtOAc/MeOH (20 mL) and stirred under a hydrogen atmosphere for 2 days. The reaction mixture was filtered through Celite, rinsed with methanol and evaporated to afford the desired compound as a colorless oil. LCMS (M+H)= 419.20.

Step E. The amino pyridine from step D was deprotected in 1:1 THF/3N HCl over 2 days at 80° C. The reaction mixture was made basic with a pellet of NaOH and concentrated. Reverse phase chromatography afforded TFA salt of the desired compound as a white solid. LCMS (M+H)=335.18. $^1$H NMR (CD$_3$OD) δ 7.84 (m, 1H), 7.16 (m, 5H), 6.96 (m, 1H), 6.89 (m, 1H), 6.80 (m, 3H), 4.32 (m, 1H), 3.79 (s, 3H), 3.74 (s, 3H), 3.43 (m, 1H), 3.35 (m, 1H).

EXAMPLE 3

6-[1-(4-methoxyphenyl)-2-phenylethyl]pyridin-2-amine

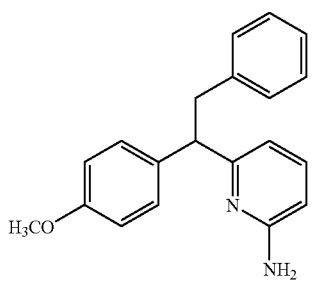

Step A. A solution of 2-dimethylaminoethanol (25.6 mL, 254 mmol) in hexane (240 ml) under nitrogen was cooled to 0° C. and n-BuLi (2.5 M, 509 mmol) was added dropwise. The solution was stirred for 30 min at 0° C., then cool to −78° C. and a solution of 2-chloropyridine (9.63 g, 84.9 mmol) in hexane (150 ml) was added drop-wise. After stirring 1 h at −78° C. 4-methoxy-N,N-dimethylbenzamide (15.2 g, 84.9) in THF (150 mL) was added dropwise, and the solution was slowly warmed to 0° C. for 1 h. The mixture was hydrolyzed at 0° C. with water (500 ml). The aqueous layer was extracted with ether then CH$_2$Cl$_2$. The organics were dried over Na$_2$SO$_4$ and purified on a silica gel column (9:1 Hexanes/EtOAc) to afford the desired ketone. $^1$H NMR (CDCl$_3$) δ 8.16 (d, J=8.9 Hz, 2H), 7.92 (d, J=7.5 Hz, 1H), 7.85 (t, J=7.6 Hz, 1H), 7.51 (d, J=6.9 Hz, 1H), 6.98 (d, J=8.9 Hz, 2H), 3.89 (s, 3H). LRMS (M+H)= 248.1

Step B. To a stirred solution of (bromomethyl)triphenylphosphonium (6.34 g, 14.5 mmol) in THF (100 mL) at −78° C. was added potassium t-butoxide (1.0M in THF, 17.4 mmol). After the mixture was stirred for 1 h at −78° C. a solution of (6-chloropyridin-2-yl)(4-methoxyphenyl)methanone (2.88 g, 11.6 mmol) in THF (5 mL) was added. The resulting mixture was allowed to stir to rt over 2 h. The reaction was quenched with water and extracted with ether (2×50 mL). Organics were combined, dried with Na$_2$SO$_4$, and purified on a silica gel column (9:1 Hexanes/EtOAc) to afford a 1.4:1 ratio of E and Z isomers . $^1$H NMR (CDCl$_3$) δ 7.71 (t, J=7.7 Hz, 1H), 7.29-7.33 (m, 2H), 7.14 (d, J=8.7 Hz, 2H), 6.82 (d, J=8.9 Hz, 2H), 6.80 (s, 1H), 3.80 (s, 3H). LRMS (M+H)=325.9

Step C. To a degassed solution of the vinylbromide from step B (22 mg, 0.068 mmol) and tributylphenyltin (25 mg, 0.068 mmol) in DMF (2 mL) was added dichlorobis (triphenylphosphine)palladium(II) (2.0 mg, 0.003 mmol). The solution was stirred under argon overnight at 85° C. The solution was cooled, filtered, and purified by reverse phase HPLC to afford the olefin. 1H NMR (CDC$_{13}$) δ 7.57 (t, J=7.7 Hz, 1H), 7.28 (d, J=7.8 Hz, 1H), 7.20 (d, J=8.7 Hz, 2), 7.10-7.18 (m, 4H), 7.06 (s, 1H), 6.95-6.98 (m, 2H), 6.86 (d, J=8.7 Hz, 2H), 3.81 (s, 3H). LRMS (M+H)=322.0

Step D. An argon filled vial was charged with the chloropyridine from step C (47 mg, 0.146 mmol), Pd$_2$(dba)$_3$ (7.0 mg, 0.007 mmol), 2-(di-cyclohexyl)phosphinobiphenyl (6.0 mg, 0.018 mmol), and LiHMDS (1.0 M in THF, 0.175 mmol) and stirred overnight at 65° C. The reaction was cooled to rt, quenched with 1N HCl and stirred for 5 minutes before it was neutralized with 1N NaOH. The mixture was extracted with CH$_2$Cl$_2$ (3×15 mL) and the combined organics were dried over Na$_2$SO$_4$, concentrated, and purified with reverse phase HPLC to provide the desired aminopyridine TFA salt. $^1$H NMR (CDCl$_3$) δ 7.68 (t, J=8.0 Hz, 1H), 7.22-7.27 (m, 5H), 7.16 (s, 1H), 7.04-7.08 (m, 2H), 6.89 (d, J=8.6 Hz, 2H), 6.67 (d, J=8.7 Hz, 1H), 6.64 (d, J=7.2 Hz, 1H), 2.08 (br s, 2H), 3.83 (s, 3H). LRMS (M+H)= 303.1

Step E. The aminopyridine from step D (21.0 mg, 0.069 mmol) was dissolved in methanol (15 mL) and treated with 10% Pd/C (10 mg). The resulting reaction was hydrogenated under a balloon of hydrogen gas for 2 h. The solution was filtered through Celite, concentrated, and purified by reverse phase HPLC to afford the desired product. 1H NMR (CDCl$_3$) δ 7.58 (t, J=8.0 Hz, 1H), 7.14-7.28 (m, 7H), 6.83 (d, J=8.7 Hz, 2H), 6.59 (d, J=7.5 Hz, 1H), 6.48 (d, J=8.7 Hz, 1H), 4.54 (t, J=8.1 Hz, 1H), 3.77 (s, 3H), 3.40-3.45 (dd, J=7.8 Hz, 1H), 3.28-3.34 (dd, J=8.4 Hz, 1H), 1.66 (br s, 2H). LRMS (M+H)=305.2

EXAMPLE 4

6-{1-phenyl-2-[4-(trifluoromethyl)phenyl]-ethyl}pyridin-2-amine

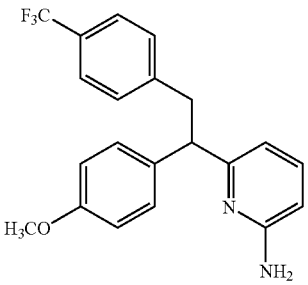

Step A: To a degassed solution of 2,6-dichloropyridine (3.65 g, 25 mmol) in THF (50 mL) was added 4-methoxybenzyl zinc chloride (50 mL of a 0.5 M THF solution, 25 mmol). Pd(PPh$_3$)$_4$ (1.0 g, 0.87 mmol) was added and the solution heated to 50° C. for 12 h. The solution was cooled and absorbed onto silica gel (30 g). Purification by silica gel chromatography (9:1 Hex/EtOAc) afforded the benzyl pyridine as a clear oil. LCMS [M+H]=234.2. $^1$H NMR (CDCl3) δ 7.51 (t, J=7.8 Hz, 1H), 7.17 (d, J=8.4 Hz, 2H), 7.14 (d, J=7.9 Hz, 1H), 6.96 (d, J=7.7 Hz, 1H), 6.85 (d, J=8.6 Hz, 2H), 4.07 (s, 2H), 3.79 (s, 3H).

Step B: To a 0° C. solution of diisopropyl amine (0.14 g, 1.35 mmol) in THF (5 mL) was added n-BuLi (0.84 mL of a 1.6 M hexane solution, 1.35 mmol). The solution was stirred at 0° C. for 20 min then cooled to −78° C. after which was added a solution of benzyl pyridine (0.3 g, 1.3 mmol) from step A in THF (5 mL). The deep red solution was stirred at −78° C. for 1 h. Alpha'-bromo-alpha, alpha, alpha-trifluoro-p-xylene (0.31 g, 1.29 mmol) was in THF (5 mL) and the solution stirred at −78° C. for 30 min. The reaction was quenched by the addition of a saturated $NaHCO_3$ solution (5 mL), extracted with EtOAc (3×20 mL), dried over $MgSO_4$, filtered and evaporated in vacuo. Purification by reverse phase HPLC afforded the alkylated chloropyridine. LCMS [M+H]=392.1. $^1$H NMR (CDCl3) δ 7.46 (t, J=7.7 Hz, 1H), 7.41 (d, J=8.1 Hz, 2H), 7.21 (d, J=8.6 Hz, 2H), 7.16 (d, J=8.1, 2H), 7.11 (d, J=7.9 Hz, 1H), 6.95 (d, J=7.5 Hz, 1H), 6.81 (d, J=8.8 Hz, 2H), 4.24 (t, J=7.8 Hz, 1H), 3.76 (s, 3H), 3.67 (dd, J=14, 7.5 Hz, 1H), 3.31 (dd, J=14, 7.9 Hz, 1H).

Step C: LiHMDS (0.15 mL of a 1.0 M THF solution, 0.15 mmol) was added to the alkylated chloropyridine (50.0 mg, 0.12 mmol) from step B, $Pd_2(dba)_3$ (6 mg, 0.006 mmol), and 2-(dicyclohexylphosphino)biphenyl (6 mg, 0.014 mmol). The reaction vessel was sealed and heated to 65° C. for 12 h. The reaction was cooled and TBAF was added (0.36 mL of a 1.0 M THF solution). The mixture was stirred for 5 min then diluted with $H_2O$ (10 mL). The solution was extracted with EtOAc (3×15 mL), dried over $MgSO_4$, filtered, and concentrated in vacuo. Purification by reverse phase HPLC afforded the desired amino pyridine. LCMS (M+H)=373.1. $^1$H NMR (CDCl$_3$) δ 7.56 (t, J=8.1 Hz, 1H), 7.44 (d, J=8.0, 2H), 7.31 (d, J=8.0 Hz, 2H), 7.24 (d, J=8.5 Hz, 2H), 6.83 (d, J=8.4 Hz, 2H), 6.68 (d, J=8.7 Hz, 1H), 6.48 (d, J=7.2 Hz, 1H), 4.49 (t, J=8.0 Hz, 1H), 3.77 (s, 3H), 3.51 (dd, J=14, 7.5 Hz, 1H), 3.32 (dd, J=14, 9.5 Hz, 1H).

The compounds of the following examples were prepared in an analogous manner to that described in the Examples above, using methods A-D as described above.

| EXAMPLE | STRUCTURE | MW | METHOD |
|---|---|---|---|
| 5 | 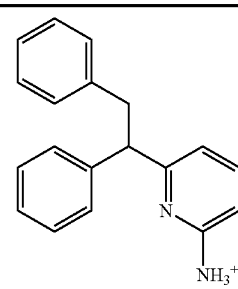 | 274.369 | A |
| 6 | 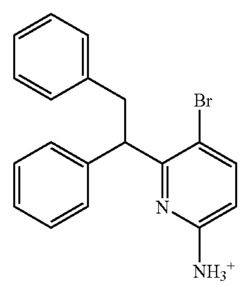 | 353.265 | A |
| 7 | 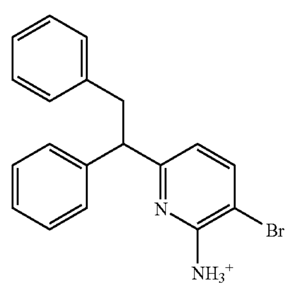 | 353.265 | A |
| 8 | 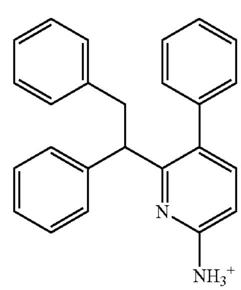 | 350.467 | A |

-continued

| EXAMPLE | STRUCTURE | MW | METHOD |
|---------|-----------|-----|--------|
| 9 | 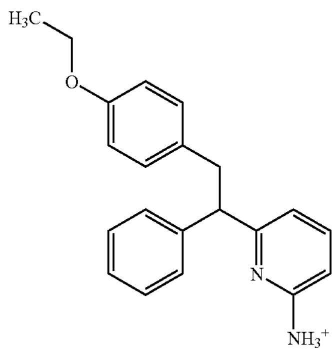 | 318.422 | C |
| 10 | 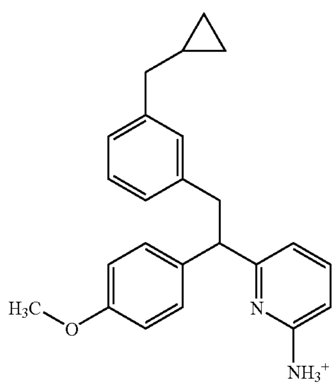 | 358.488 | D |
| 11 | 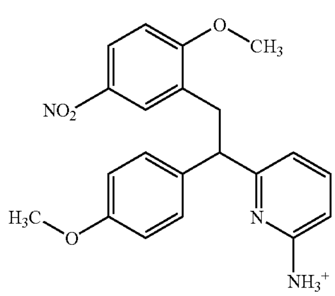 | 379.419 | D |
| 12 | 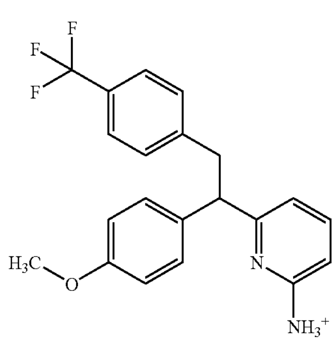 | 372.394 | D |

-continued
| EXAMPLE | STRUCTURE | MW | METHOD |
|---|---|---|---|
| 13 | 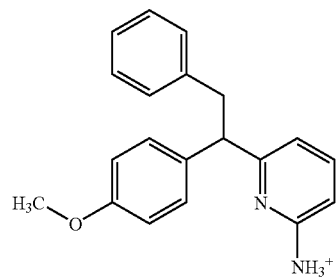 | 304.395 | D |
| 14 | 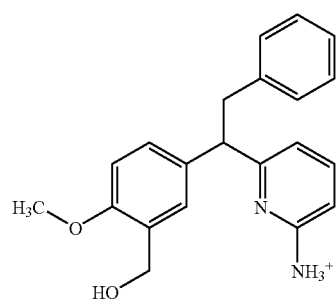 | 334.422 | B |
| 15 | 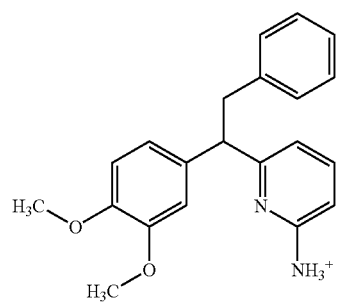 | 334.422 | B |
| 16 | 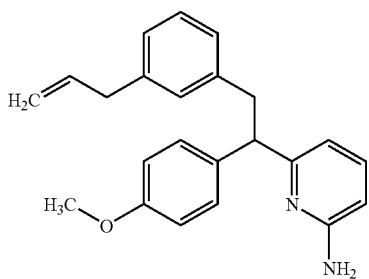 | 344.461 | D |
| 17 | 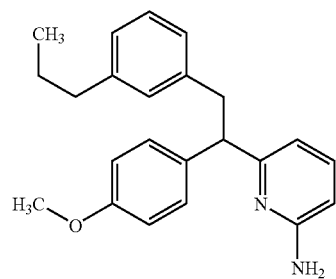 | 346.476 | D |

-continued

| EXAMPLE | STRUCTURE | MW | METHOD |
|---|---|---|---|
| 18 | 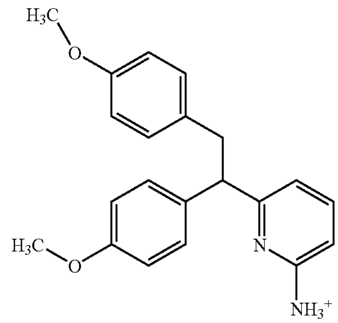 | 334.422 | C |
| 19 | 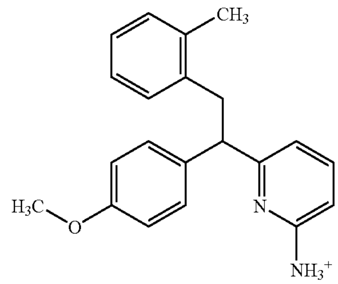 | 318.422 | C |

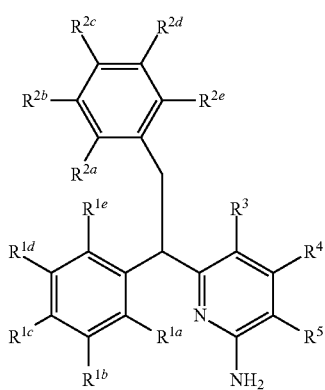

While some of the compounds depicted in the table above are represented in their acid form, the invention is intended to encompass both the salt and free base forms of the compounds described above.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:
1. A compound of formula (II)

(II)

wherein:
$R^{1a}$, $R^{1b}$, $R^{1c}$, $R^{1d}$ and $R^{1e}$ are selected from the group consisting of:

(1) hydrogen,
(2) halogen,
(3) cyano,
(4) —$C_{1-6}$ alkyl, wherein said alkyl is unsubstituted or substituted with one or more hydroxyl, halogen, or $NH_2$,
(5) —$OR^{7a}$,
(6) —C(=O)—$NR^{7a}R^{7b}$,
(7) —NH—C(=O)—$R^{7a}$,
(8) —N—$R^{7a}R^{7b}$,
(9) —S(=O)$_p$—$R^{8a}$,
(10) —$NR^{7a}$—S(=O)$_p$—$R^{8a}$,
or $R^{1c}$ and $R^{1d}$ are linked together to form the group —OCH$_2$CH$_2$O— or —OCH$^2$CH$^2$—;

$R^{2a}$, $R^{2b}$, $R^{2c}$, $R^{2d}$ and $R^{2e}$ are selected from the group consisting of:
(1) hydrogen,
(2) halogen,
(3) cyano,
(4) hydroxyl,
(5) —$C_{0-6}$ alkyl-$C_{3-8}$ cycloalkyl
(6) —$C_{1-6}$ alkyl, wherein said alkyl is unsubstituted or substituted with one or more halogen or hydroxyl,
(7) —$C_{2-6}$ alkenyl,
(8) —O—$R^{7a}$,
(9) —C(=O)—$R^{7a}$
(10) —$NO_2$,
(11) $C_{6-10}$ aryl, wherein said aryl can be unsubstituted or substituted with one or more
(a) halogen,
(b) cyano,
(c) —$C_{1-6}$ alkyl,
(d) —$C_{1-6}$ alkoxy,
(e) —C(=O)—O—$R^{7a}$,
(f) —C(=O)—$R^{7a}$,
(g) —$NR^{7a}R^{7b}$,
(h) —$NR^{7a}$—S(=O)$_p$—$R^{8a}$,
(i) —$NR^{7a}$—C(=O)—$R^{7b}$, (j) —$NO_2$
(k) heteroaryl selected from the group consisting of furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, indazolyl, benzimidazolyl, quinolyl and isoquinolyl,
wherein said heteroaryl is unsubstituted or substituted with one or more halogen, —$C_{1-6}$ alkyl, —$C_{1-6}$ alkoxy, hydroxy or cyano,
or $R^{2c}$ and $R^{2d}$ are linked together to form a group —$CR^{7a}R^{7b}CR^{7c}R^{7d}CR^{7e}R^{7f}$—, —$OCH_2CH_2O$— or —$OCH^2CH^2$—, and $R^3$, $R^4$ and $R^5$ are independently selected from the group consisting of:
(1) hydrogen
(2) -($Q^2$)$_n$—$R^9$
(3) heteroaryl wherein said heteroaryl is selected from the group consisting of furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, indazolyl, benzimidazolyl, quinolyl and isoquinolyl,
(4) —$C_{6-10}$ aryl
(5) a carbocyclic group having from 3 to 8 ring atoms, optionally having (i) a —C(=O)— ring atom, (ii) from one to three ring heteroatoms selected from the group consisting of S, N and O, and (iii) a single carbon-carbon double bond,
(6) halogen,
(7) cyano,
(8) —$N_3$,
(9) —$NO_2$,
(10) —$OR^{7a}$
wherein $R^9$ is selected from the group consisting of
(a) —$C_{1-10}$ alkyl,
(b) —$C_{0-3}$ alkyl-$C_{3-8}$ cycloalkyl,
(c) —$C_{2-10}$ alkenyl,
(d) —$C_{2-10}$ alkynyl,
(e) —$C_{3-10}$ cycloalkenyl, and
(f) —$C_{3-10}$ cycloalkynyl, and
$Q^2$ is selected from the group consisting of O, S, $NR^{7a}$,—(C=O)—O—, —$NR^{7a}$—S(=O)$_p$—S(=O)$_p$,—C(=O)—$NR^{7a}$, —$NR^{7a}$—C(=O)—,
wherein said $R^9$ alkyl, alkenyl, alkynyl, cycloalkyl, cycloalkenyl, cycloalkynyl, carbocyclic, aryl and heteroaryl groups are unsubstituted or substituted with one or more,
(a) halogen,
(b) cyano,
(c) —$C_{1-6}$ alkyl,
(d) —$C_{2-6}$ alkenyl,
(e) —$C_{2-6}$ alkynyl,
(f) —$OR^{7a}$
(g) —C(=O)—O—$R^{7a}$,
(h) —C(=O)—$R^{7a}$,
(i) —C(=O)—$NR^{7a}R^{7b}$,
(j) —$NR^{7a}R^{7b}$,
(k) —$NR^{7a}$—S(=O)$_p$—$R^{7b}$,
(l) —$NR^{7a}$—C(=O)—$R^{7b}$,
(m) —$NO_2$,
(n) —$CH_2$—$C_{6-10}$ aryl,
(o) —$C_{6-10}$ aryl,
(p) heteroaryl,
(q) —$C_{3-8}$ cycloalkyl
(r) —C(=O)—N—$SO_2R^{8a}$, and said $R^9$ alkyl, alkenyl and alkynyl groups are optionally interrupted with one or more $Q^2$ groups,
$R^{7a}$, $R^{7b}$, $R^{7c}$, $R^{7d}$, $R^{7e}$ and $R^{7f}$ are selected from the group consisting of:
(1) hydrogen,
(2) —$C_{1-6}$ alkyl,
(3) —$C_{3-8}$ cycloalkyl
(4) —$C_{6-10}$ aryl, and
(5) —$CH_2$—$C_{6-10}$ aryl;
provided that when $R^{7a}$ and $R^{7b}$ are bound to the same N atom, then $R^{7a}$ and $R^{7b}$ may form a four to five hydrocarbon chain with the N atom to which they are attached to form a carbocyclic ring having a single N atom;
wherein said $R^{7a}$—$R^{7f}$ alkyl, cycloalkyl or aryl groups are unsubstituted or substituted with one or more halogen, —$C_{1-6}$alkyl,—$C_{1-6}$alkoxy, hydroxyl, cyano or a carbocyclic group having from 3 to 8 ring atoms, optionally having (i) a —C(=O)— ring atom, (ii) from one to three ring heteroatoms selected from the group consisting of S, N and O, and (iii) a single carbon-carbon double bond;
$R^{8a}$ is selected from the group consisting of
(1) —$C_{1-6}$ alkyl,
(2) —$C_{6-10}$ aryl, and
(3) —$CH_2$—$C_{6-10}$ aryl;
wherein said $R^{8a}$ alkyl or aryl groups are unsubstituted or substituted with one or more halogen, —$C_{1-6}$alkyl, —$C_{1-6}$alkoxy, hydroxyl or cyano;
n is 0 or 1;
p is 0, 1 or 2;
and pharmaceutically acceptable salts thereof, and individual enantiomers and diastereomers thereof.

2. The compound of claim 1, wherein $R^{1a}$, $R^{1b}$, $R^{1c}$, $R^{1d}$ and $R^{1e}$ are selected from the group consisting of:
(a) hydrogen,
(b) halogen,
(c) —$OR^{8a}$ wherein $R^{8a}$ is $C_{1-6}$ alkyl, and
(d) —$CH_2OH$.

3. The compound of claim 2, wherein $R^{1a}$, $R^{1d}$ and $R^{1e}$ are hydrogen, and $R^{1b}$ and $R^{1c}$ are independently selected from the group consisting of:
(a) hydrogen,
(b) halogen,
(c) —$OR^{8a}$ wherein $R^{8a}$ is $C_{1-6}$ alkyl, and
(d) —$CH_2OH$.

4. The compound of claim 1, wherein $R^{2a}$, $R^{2b}$, $R^{2c}$, $R^{2d}$ and $R^{2e}$ are selected from the group consisting of:
(1) hydrogen,
(2) —$C_{1-6}$ alkyl, wherein said alkyl is unsubstituted or substituted with one or more halogen,
(3) —O—$R^{7a}$, wherein $R^{7a}$ is $C_{1-6}$ alkyl,
(4) —$NO_2$,
(5) —$C_{2-6}$ alkenyl,
(6) —$C_{1-6}$ alkyl—$C_{3-6}$ cycloalkyl.

5. The compound of claim 1 wherein $R^{2a}$, $R^{2b}$, $R^{2c}$, $R^{2d}$ and $R^{2e}$ are each hydrogen.

6. The compound of claim 1 wherein $R^3$, $R^4$ and $R^5$ are independently selected from the group consisting of:
(1) hydrogen
(2) $C_{1-10}$ alkyl
(3) $C_{6-10}$ aryl, and
(4) halogen.

7. The compound of claim 1 wherein $R^3$, $R^4$ and $R^5$ are each hydrogen.
8. A compound of claim 1 which is selected from the group consisting of
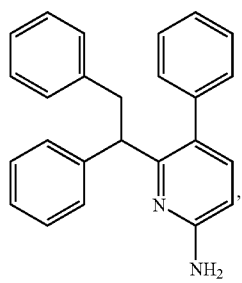,
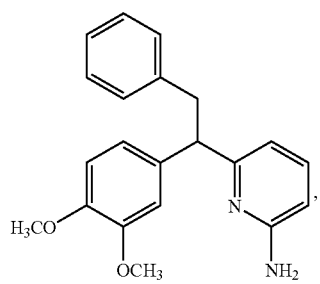,
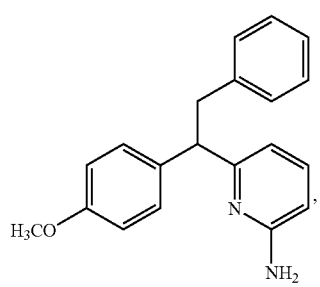,
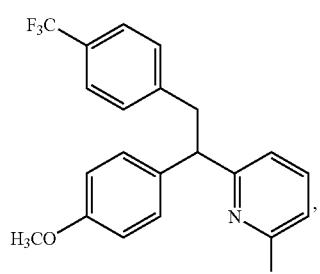,
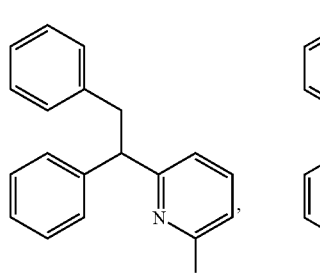,
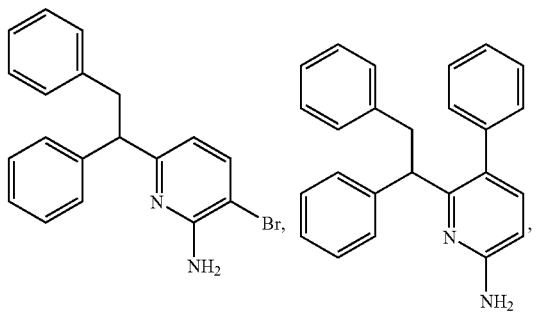,
-continued
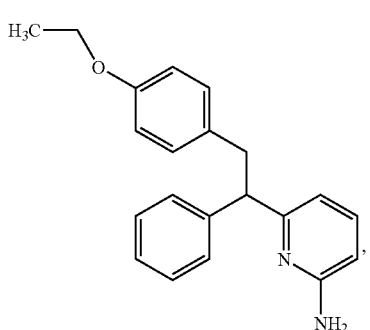,
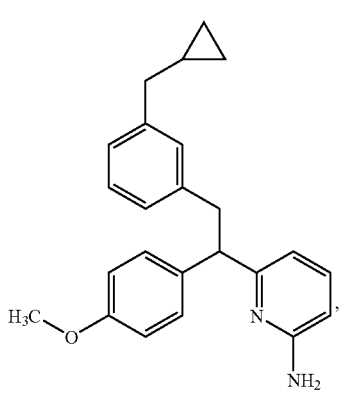,
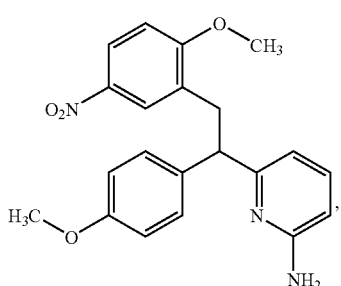,
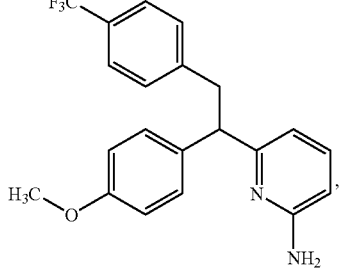,

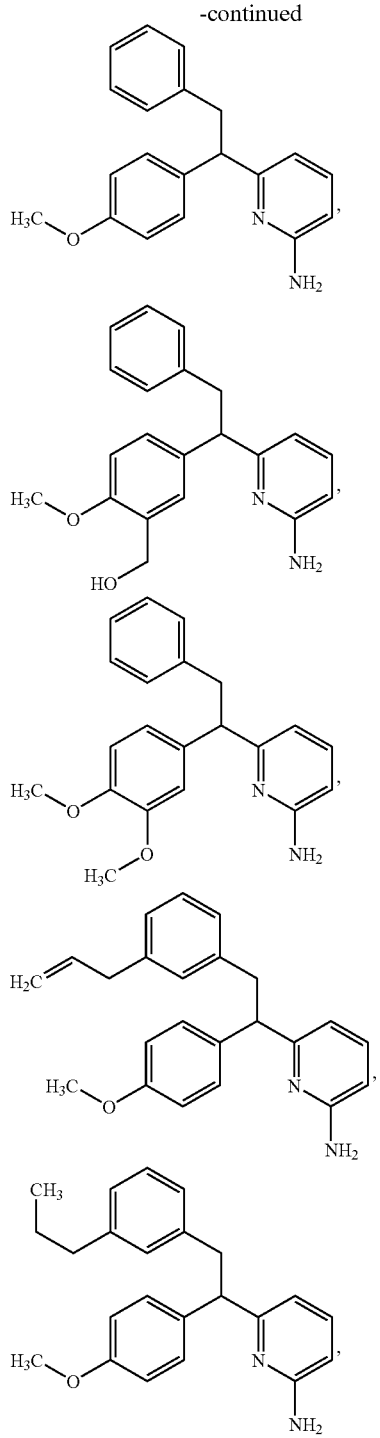

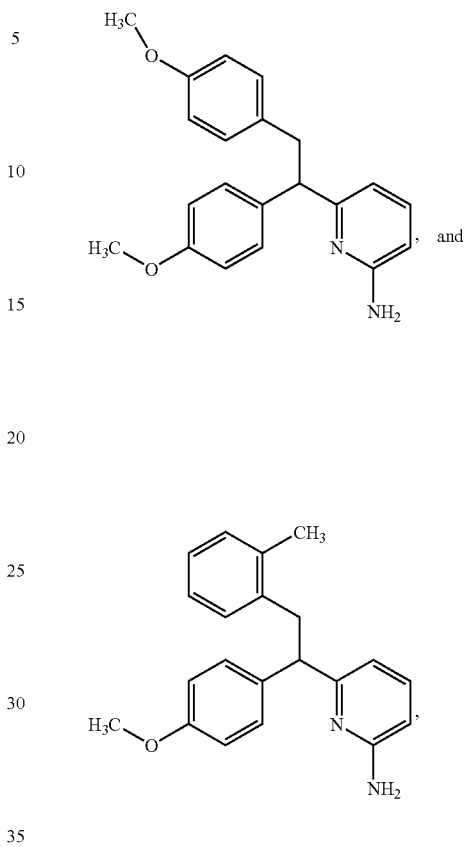

and pharmaceutically acceptable salts thereof.

9. The pharmaceutical composition comprising a therapeutically effective amount of a compound of claim 1 or a pharmaceutically acceptable salt thereof and a pharmaceutically acceptable carrier.

10. The method for inhibition of β-secretase activity in a mammal in need thereof which comprises administering to the mammal a therapeutically effective amount of a compound of claim 1 or a pharmaceutically acceptable salt thereof.

11. A method for treating Alzheimer's disease in a patient in need thereof comprising administering to the patient a therapeutically effective amount of a compound of claim 1 or a pharmaceutically acceptable salt thereof.

* * * * *